United States Patent [19]

Dufour

[11] Patent Number: 4,457,708
[45] Date of Patent: Jul. 3, 1984

[54] MANDIBULAR STABILIZER

[76] Inventor: Gerald Dufour, 2935 Longchamp St., Ste-Foy, Quebec G1W 2G2, Canada

[21] Appl. No.: 369,608

[22] Filed: Apr. 19, 1982

[30] Foreign Application Priority Data

Feb. 8, 1982 [CA] Canada ................................ 395721

[51] Int. Cl.³ ................................................ A61C 7/00
[52] U.S. Cl. ..................................... 433/6; 128/76 R
[58] Field of Search ................. 433/6; 128/62 A, 136, 128/76 R, 68

[56] References Cited

U.S. PATENT DOCUMENTS

| | | |
|---|---|---|
| 2,467,432 | 7/1943 | Kesling . |
| 3,334,417 | 8/1967 | Spengeman ............................ 433/6 |
| 3,478,429 | 5/1968 | Shilliday . |
| 3,837,081 | 9/1974 | Kesling . |
| 3,848,335 | 11/1974 | Bergersen . |
| 3,898,736 | 8/1975 | Bergersen . |
| 4,055,895 | 11/1977 | Huge . |
| 4,073,061 | 2/1978 | Bergersen . |
| 4,139,944 | 2/1979 | Bergersen . |
| 4,211,008 | 7/1980 | Lerman ..................................... 433/6 |
| 4,253,828 | 3/1981 | Coles et al. . |

FOREIGN PATENT DOCUMENTS

| | | |
|---|---|---|
| 158966 | 11/1914 | Canada . |
| 467603 | 8/1950 | Canada . |
| 744195 | 10/1966 | Canada . |
| 745435 | 11/1966 | Canada . |
| 796051 | 10/1968 | Canada . |

*Primary Examiner*—Robert Peshock
*Attorney, Agent, or Firm*—Bradford E. Kile

[57] ABSTRACT

The invention is an oral orthopedic appliance for relieving maxillo-mandibular imbalance. The appliance comprises in its simplest form an arcuate preformed portion of a unitary size and shape, adapted to fit all size mandibles, and a pair of moulded portions, each moulded portion extending from an end of the preformed portion and being adapted to fit the wearer of the appliance. The preformed portion in use extends adjacent a side of the mandibular teeth and overlies the mandibular molar or premolar teeth, or both; the moulded portion is bonded to the preformed portion and is shaped to the contour of the top surface of the mandibular molar or premolar teeth, or both. A means for relieving maxillo-mandibular imbalance by means of such an appliance is also disclosed.

22 Claims, 19 Drawing Figures

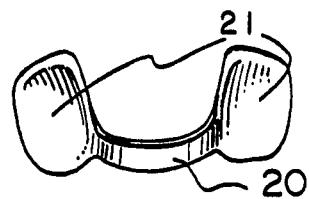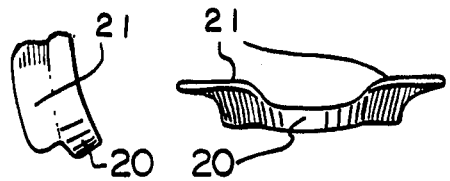
FIG.1  FIG.2  FIG.3
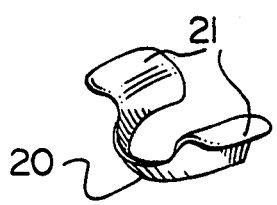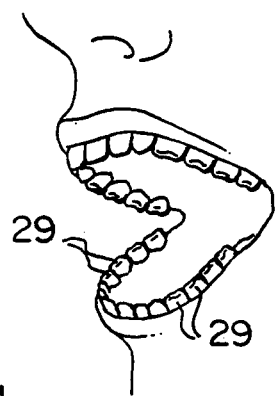
FIG.4  FIG.8
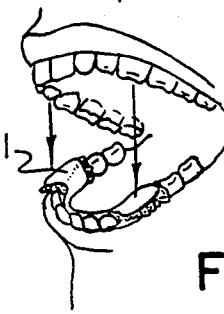
FIG.5  FIG.6  FIG.9
FIG.7
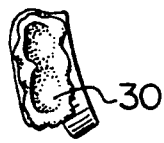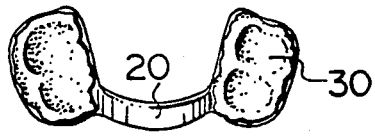
FIG.10  FIG.11
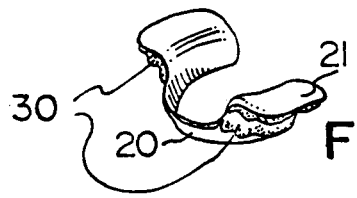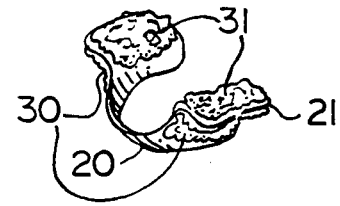
FIG.12  FIG.13

MANDIBULAR STABILIZER

This invention relates to an oral orthopedic appliance for relieving maxillo-mandibular imbalance and, more particularly, to such an appliance that is easily-fitted and can be worn inconspicuously.

Humans normally have an outgrowth of 32 permanent teeth, 16 in the upper jaw and 16 in the lower jaw (the "mandible"), including the four wisdom teeth. For various reasons, some individuals have an outgrowth of a lesser number of teeth. Also, the majority of people lose some or all of their teeth during their lifetime, necessitating the use of implants, bridges, plates or dentures. It has recently become recognized that a misalignment of the mandible relative to the upper jaw that may result, for example, from loss of either some of the upper and lower posterior teeth, or both, may be responsible for a physiological dysfunction that may manifest itself in various ways throughout the body; this dysfunction has been given the name "The Dysgnathogenic Distress Syndrome" by some, "The Cranio-Mandibular Syndrome" by others.

The mandible is connected to the cranium by means of the temporo-mandibular joints, located immediately in front of the ears, rotation about those joints being by means of the masticatory muscles, each of which extends from an opposite side of the mandible to a connecting point on the cranial bones. The masticatory muscles have an "at rest" position intermediate of their extended and contracted states. In persons having a proper outgrowth of a full complement of teeth, the mandibular portion of each temporo-mandibular joint will rest lightly in the cranial portion of the joint and each of the muscles, as mentioned, will be in their physiological "relaxed" or "at rest" position.

The "Dysgnathogenic Distress Syndrome" is a term that relates among other things to neuralgias and cephalgias whose origin have been generally linked to misalignment of the mandible relative to the upper jaw and cranium which results from either a lack of some or all of the rear teeth or improper growth of those teeth. If the rear teeth are either missing or mispositioned the masticatory muscles will assume an "at rest" position in which they will be slightly contracted from the physiologically-normal position; also, the mandibular ball portions of the temporo-mandibular joints will be pressed deeper into their cranial sockets than is physiologically normal. It has been found that the symptoms of the "Dysgnathogenic Distress Syndrome" might be relieved when a splint is placed between the teeth to reposition the mandible relative to the cranium, the repositioning allowing the masticatory muscles and the temporo-mandibular joint to assume their physiologically-normal position.

The subject invention is an oral orthopedic appliance which can be fitted between the upper and lower premolar or molar teeth, or both, to reposition the mandible and relieve the symptoms of the "Dysgnathogenic Distress Syndrome", which symptoms can manifest themselves throughout the various parts of the body. After the appliance is positioned in the mouth to space the mandibular teeth from those in the upper jaw any under-erupted posterior teeth are given a chance to grow into the spacing. An advantage of the appliance is that it inconspicuously sits between the upper and lower premolar or molar teeth, or both, along one side of the lower front teeth.

In one form, the invention is an orthopedic appliance for relieving maxillo-mandibular imbalance, comprising an acrylic preformed structure having an arcuate first portion adapted to extend along and be adjacent to the surface of the mandibular teeth, and two flange portions, each integrally connected to a respective end section of the first portion and adapted to overlie the tops of a respective set of either the mandibular premolar teeth or the mandibular molar teeth, or both. The flange portions are disposed when in use between such set of mandibular teeth and the corresponding teeth in the upper jaw, so as to provide a selected spacing between the mandible and the upper jaw and, over an extended period of use, to provide for stabilization and normalization of the position of the mandible relative to the upper jaw. The oral orthopedic appliance further comprises two moulded inserts, each bonded to a respective one of the flange portions and adapted to extend from that flange portion toward the respectively associated set of mandibular teeth. The surface contour on each insert corresponds to the surface contour on the respectively associated set of mandibular teeth.

In an alternate form, the oral orthopedic appliance may comprise the aforementioned preformed structure and two mouldable inserts, each of which inserts is bonded to a respective one of the flange portions of the structure and is adapted to extend from that flange portion toward the respectively associated set of mandibular teeth. Each of the inserts is adapted to be moulded under gentle pressure to create therein a surface contour corresponding to that on the respectively associated set of mandibular teeth.

The arcuate first portion of the preformed structure may extend along the inner surface of the mandibular teeth during use and the preformed structure may be of a unitary size and shape adapted to fit all wearers of the appliance The preformed structure of the appliance may be formed from acrylic.

In a further form, the oral orthopedic appliance of the subject invention may comprise a mouldable structure having an arcuate first portion adapted to extend along and be adjacent to the surface of the mandibular teeth, and two flange portions, each integrally connected to a respective end section of the first portion and adapted to overlie the tops of a respective set of the mandibular premolar teeth or the mandibular molar teeth, or both. Each flange portion is adapted to be moulded under gentle pressure to create therein a surface contour corresponding to that on the respectively associated set of mandibular teeth. The flange portions, when adapted for use, are disposed between such set of mandibular teeth and the corresponding teeth in the upper jaw, and provide a selected spacing between the mandible and the upper jaw, and over an extended period of use, provide for stabilization and normalization of the position of the mandible relative to the upper jaw.

In yet further forms of the invention, the orthopedic appliance of the subject invention may have an additional insert bonded to each one of the respective flange portions which insert may be adapted to extend from that flange portion toward the respectively associated set of teeth in the upper jaw. Alternatively, each flange portion may be adapted to be moulded under gentle pressure and in such case, a surface contour corresponding to that on a respectively associated set of mandibular teeth will be created in one surface of that flange portion and a surface contour corresponding to that on the respectively associated set of teeth in the upper jaw will be created in the opposite surface of that flange portion.

In a yet further form, the invention is a method for relieving maxillo-mandibular imbalance by repositioning of the lower jaw relative to the upper jaw, which initially comprises the step of spreading a malleable polymer mixture onto the flange portions of a flexible, preformed structure having an arcuate first portion and two flange portions, each flange portion being integrally connected to a respective end section of the first portion. The next step in the method involves inserting the preformed structure between the jaws, the structure being positioned such that the arcuate first portion extends along and is adjacent to the surface of the mandibular teeth, and the malleable polymer mixture on each flange portion rests on a respective set of the mandibular premolar teeth or the mandibular molar teeth, or both. A further step involves closing the jaws to conform the shape of the malleable polymer mixture to the shape of the biting surfaces of the respective sets of mandibular teeth and to promote bonding between the preformed structure and the malleable polymer mixture. A further step involves removing the preformed structure with the malleable polymer mixture bonded thereto after commencement of hardening of the mixture, the mixture surfaces retaining the contour of the biting surfaces of the respective sets of mandibular teeth. A final step involves periodically reinserting the structure between the jaw to rest on the respective sets of mandibular teeth after hardening of the mixture.

The foregoing method may alternately embody different initial steps. The malleable polymer mixture may be first spread over each set of mandibular premolar teeth or mandibular molar teeth, or both. Next, the flexible, preformed structure may be inserted between the jaws such that the arcuate first portion extends along and is adjacent to the surface of the mandibular teeth and each flange portion rests on the malleable polymer mixture over a respective set of the mandibular teeth. The jaws would then be closed to conform the shape of the malleable polymer mixture to the shape of the biting surfaces of the respective sets of mandibular teeth, as in the previously-described method.

Prior to the step of periodically reinserting the structure between the jaws, the method may involve additional steps. Firstly, a further amount of the malleable polymer mixture may be spread onto the other side of each flange portion of the flexible, preformed structure from that side on which polymer mixture was first placed. The jaws may then be closed to conform the shape of the further amount of the malleable polymer mixture to the shape of the biting surfaces of the corresponding teeth on the upper jaw and to promote bonding between the preformed structure and the further amount of the malleable polymer mixture. The final additional step involves removing the preformed structure with the further amount of the malleable polymer mixture bonded thereto after commencement of hardening of that further amount of mixture, the surfaces of that further amount of mixture retaining the contour of the biting surfaces of the corresponding teeth on the upper jaw.

The invention will now be more fully explained by means of a description and drawings of a preferred embodiment, in which drawings:

FIG. 1 is a bottom view of the preformed structure of the orthopedic appliance.

FIG. 2 is a side view of the preformed structure of the orthopedic appliance.

FIG. 3 is an end view of the preformed structure of the orthopedic appliance, the arcuate first portion being more proximate in the view.

FIG. 4 is a perspective view of the preformed structure of the orthopedic appliance.

FIG. 5 is a perspective view of an alternate embodiment of the preformed structure of the orthopedic appliance.

FIG. 6 is a perspective view of a further alternate embodiment of the preformed structure of the orthopedic appliance.

FIG. 7 is a bottom view of the preformed structure of the orthopedic appliance after placement of the hardenable paste on the flanges of the structure and prior to insertion of such preformed structure in the patient's mouth.

FIG. 8 is a view of a patient's mouth prior to fitting of the orthopedic appliance.

FIG. 9 is a view of the patient's mouth as in FIG. 8 and additionally showing positioning of the preformed structure of FIG. 7 in the patient's mouth prior to application of the moulding pressure.

FIG. 10 is a side view of the preformed structure of the orthopedic appliance of FIG. 7 after moulding of the inserts bonded thereto.

FIG. 11 is a bottom view of the preformed structure of the orthopedic appliance of FIG. 7 after moulding of the inserts bonded thereto.

FIG. 12 is a perspective view of the preformed structure of the orthopedic appliance of FIG. 7 after moulding of the inserts bonded thereto.

FIG. 13 is a perspective view of the preformed structure and bonded inserts of FIG. 12 and illustrating additional moulded inserts bonded to the other sides of the flange portions.

Figure 16:
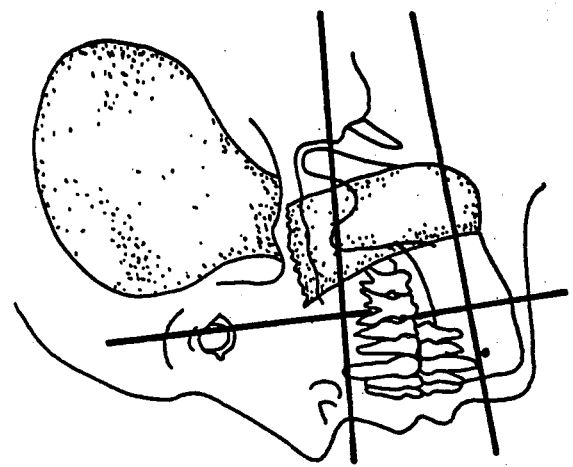
FIG. 16 is a sectioned side view of the front portion of the head illustrating misalignment of the mandible relative to the upper jaw resulting from loss of posterior teeth.

A preferred embodiment of the invention will next be described utilizing the accompanying drawings.

The structure illustrated in FIGS. 1 to 4 inclusive is injection-moulded from acrylic and has an arcuate first portion 20 from the end sections of which extend integral flange portions 21. The structure is mass-produced in a unitary size and shape and dimensioned such that portion 20 is positioned to extend adjacent to the inner surface of the mandibular teeth when flange portions 21 extend from the end sections of arcuate portion 20 to overlie the top surface of the mandibular premolar teeth of most wearers. FIG. 5 illustrates an alternative embodiment in which the structure is proportioned such that flange portions 22 extend from the end sections of an extended arcuate portion 23 to overlie the top surface of the molar teeth of most wearers. FIG. 6 illustrates a further alternative embodiment in which the structure of FIG. 5 has extended flange portions 24 to overlie the top surface of both the molar and premolar teeth of most wearers.

FIGS. 5 to 7 illustrate the steps in constructing the orthopedic appliance, utilizing one of the acrylic preformed structures that would fit over the mandibular premolar teeth only. A small amount of orthodontic resin is mixed into a paste which is placed onto the flange portions of the preformed structure, as illustrated in FIG. 7, prior to insertion of that structure into the patient's mouth of FIG. 8. The preformed structure with the paste (28 in FIG. 7) on its flanges is next inserted into the patient's mouth such that the paste extends between each flange portion and the respectively associated set of mandibular premolar teeth 29 while the arcuate first portion 20 of the structure extends along the inner surface of the mandibular teeth as illustrated in FIG. 9. The orthodontic resin that comprises the paste is a standard hardenable acrylic which is well-known to dental practitioners and has a hardening time of approximately 5 minutes. Once the structure has been properly positioned in the mouth the patient is guided to take a moderate bite and to maintain the appliance (i.e. the preformed structure and hardening paste) between his teeth until the paste is nearly hardened at the proper new position; the appliance will be very difficult to remove if allowed to remain in the mouth until the paste fully hardens.

Once formed, the orthopedic appliance has a shape similar to that illustrated in FIGS. 10 to 12 inclusive. As shown in those drawings, the hardened paste 30 which has bonded to flanges 21 has assumed a surface contour matching the contour on the top of the premolar teeth of the patient. It is necessary to file off from the orthopedic appliance any excess hardened paste extending beyond the contour of the premolar teeth; the excess paste would be that which flowed out from under the flanges when pressure was applied to shape the appliance. The appliance might be worn 24 hours a day although it may be removed for cleaning purposes; some patients will also prefer to remove the appliance before eating.

The alternative preformed structures of FIGS. 5 and 6 could be utilized to form similar appliances fitting over the mandibular molar teeth or both the mandibular molar and premolar teeth, respectively.

FIG. 13 illustrates a further embodiment of the orthopedic appliance of the subject invention in which additional hardenable paste 31 has been placed onto the other side of each flange portion of the orthopedic appliance of FIG. 12 and a contour created in the paste of the respectively associated set of teeth in the upper jaw. Such further embodiment could also utilize the alternative preformed structures of FIGS. 5 and 6.

The total length of time during which the appliance will be worn is dependent upon several factors. One factor is the patient's particular dental state when the treatment is initiated. This will be further discussed with reference to FIGS. 14 to 19, inclusive.

Figure 14:
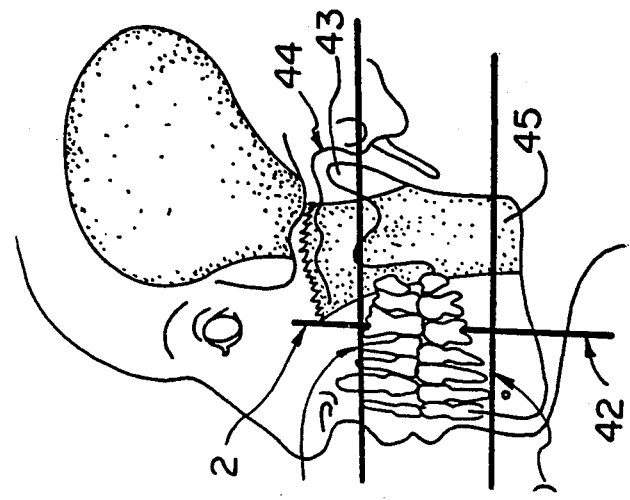
FIG. 14 is a sectioned side view of the front portion of the head illustrating the normal physiological placement of the mandible relative to the upper jaw.

FIG. 14 illustrates a sectioned side view of the front portion of the head of a person whose mandible is in proper alignment with the upper jaw. Notice that the illustrated inferior horizontal plane 40 and superior horizontal plane 41 are parallel and that the transverse plane 42 is perpendicular to both the horizontal planes 40 and 41. The mandibular ball portion 43 of the person's left temporo-mandibular joint rests lightly in the corresponding cranial socket 44, while the person's left masticatory muscle 45 is in a physiologically "relaxed" or "at rest" position, what can be referred to as the "physiologically-normal" state. Deviations from the proper alignment between the mandible and the upper jaw are illustrated in FIGS. 15, 16 and 17.

Figure 15:
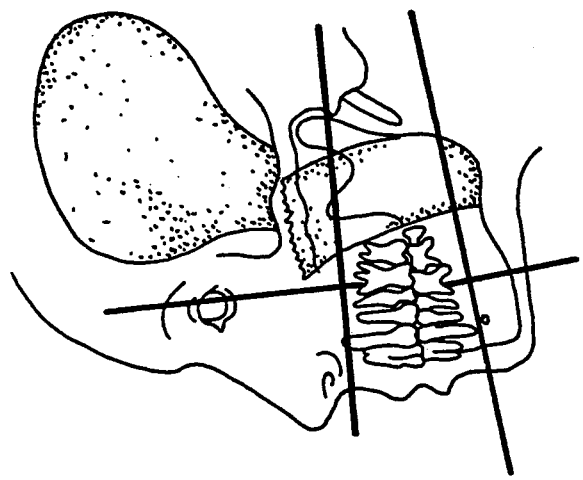
FIG. 15 is a sectioned side view of the front portion of the head illustrating misalignment of the mandible relative to the upper jaw resulting from under-eruption of the posterior teeth.

FIG. 15 illustrates a deviation from proper alignment between the mandible and the upper jaw resulting from under-eruption of the posterior teeth (i.e. molar teeth or premolar teeth, or both). Without proper support from the posterior teeth, each masticatory muscle 45 assumes a position slightly contracted from the physiologically-normal postion illustrated in FIG. 14. The mandibular ball portions 43 of the person's temporo-mandibular joints rest more heavily in their cranial sockets than in the physiologically-normal state illustrated in FIG. 14. In this condition, the inferior horizontal plane 40 inclines rearwardly toward the superior horizontal plane 41 and the plane 42, which is transverse to the horizontal plane, assumes a curvature. A person with this condition might appear to have a forward tilt to their head. Apart from appearance, it has been found in studies that persons with this condition might experience various localized pains and other dysfunctions throughout their body as compared to a person having the mandible in the physiologically-normalized position of FIG. 14. One theory is that the shortened masticatory muscles and tight temporo-mandibular joints place pressure on the cranium which in turn exerts pressure on various regions of the brain. The mechanism of jaw repositioning might follow the osteopathic cranial concept of corrective techniques advocated by the osteopathic profession. Whatever the mechanism, it has been found that restoring parallelism between the inferior and superior horizontal planes might result in a marked decrease in the pain experienced in various parts of the body and in a normalization of numerous organic functions of the body.

Figure 17:
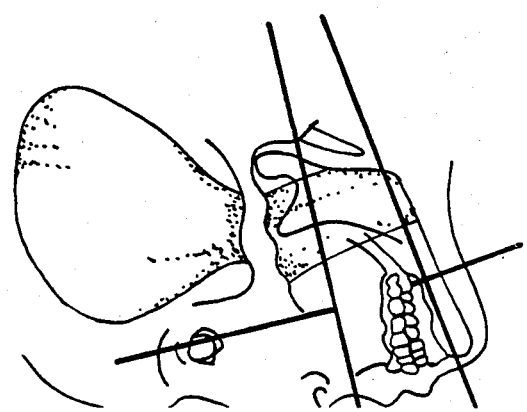
FIG. 17 is a sectioned side view of the front portion of the head illustrating misalignment of the mandible relative to the upper jaw resulting from loss of all the teeth, and replacement by complete dentures.

As well as under-eruption of the posterior teeth, loss of some or all of the posterior teeth may cause the mandible to move out of alignment with the upper jaw; this is illustrated in FIG. 16. As illustrated in FIG. 17, loss of all teeth will result in a severe misalignment between the mandible and the cranium. The superior horizontal plane in this case is more sharply inclined than in the case of loss of posterior teeth only, and with this condition there might be a severe tilting of the head.

Figure 18:
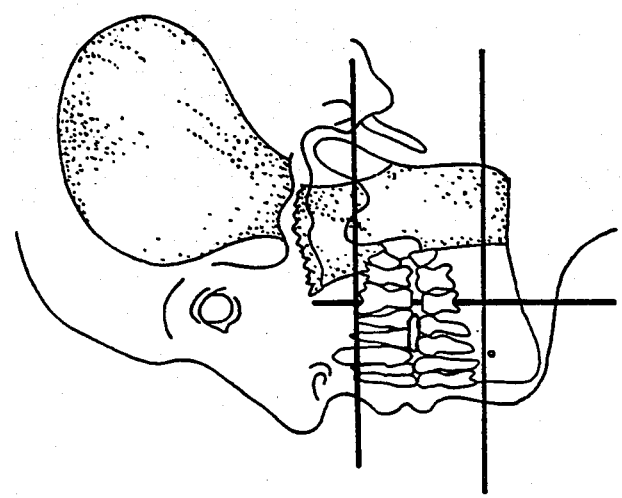
FIG. 18 is a sectioned side view of the front portion of the head illustrating the under-erupted posterior teeth of FIG. 15, and additionally illustrating placement of the orthopedic appliance of the subject invention between the upper and lower premolar teeth.

The orthopedic appliance of this invention is worn in the mouth of a patient with its flanges spacing the mandible from the upper jaw, as shown in FIG. 18; in that illustration, the appliance is resting between the under-erupted posterior teeth of FIG. 15. The flanges could also rest between the remaining upper and lower posterior teeth of a person having some posterior teeth loss, as in FIG. 16, or between the middle or posterior portions of a lower denture where there has been complete loss of teeth, as in FIG. 17.

In a case where some of the posterior teeth have been lost only, it should be possible after a period of wear of the device and after the mandible has resumed its physiologically-normal position, to fit a bridge or partial denture or "overlay" into the posterior region to maintain the mandible in that physiologically-normal position and to discontinue wearing of the appliance. In the case of under-erupted posterior teeth and side shifting of teeth, it might also be possible to utilize orthodontic measures particularly with functional orthodontics instead of or in conjunction with utilizing a bridge or partial denture or "overlay".

Figure 19:
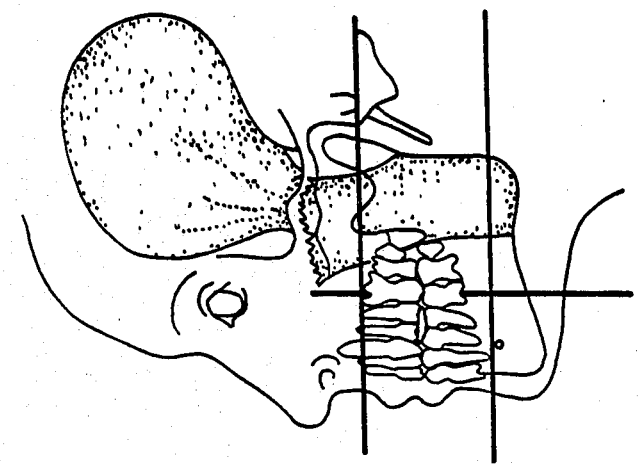
FIG. 19 is a sectioned side view of the front portion of the head as in FIG. 18, and additionally illustrating a subsequent eruption of teeth posterior thereto.

A person having under-erupted posterior teeth will be able to discontinue wearing of the appliance once those posterior teeth, either naturally or by orthodonic coaxing, have extended into the spacing between those posterior teeth that results from wearing of the appliance. Eruption of the under-erupted posterior teeth of FIG. 18 is illustrated in FIG. 19. Once the spacing between the posterior teeth has been closed, the mandible is maintained in its physiologically-normal position; once the appliance is removed, the teeth on which the applicance has been positioned have freedom to erupt to fill the spacing formerly occupied by the flanges of the appliance.

A clinical study that was completed in 1980 indicated that wearing of the orthopedic appliance dramatically reduced the localized body pains that had been experienced among persons having the "Dysgnathogenic Distress Syndrome". The localized pains that disappeared included facial neuralgias, headaches, earaches, blurred vision and other eyesight problems, soreness in the throat, and pains in other parts of the body, including the back, neck, shoulders, hips, hands, fingers, and feet. As mentioned, it is not fully understood why misalignment between the mandible and the cranium results in localized pain throughout the body, but it is believed that the misalignment places pressure on the cranium which in turn affects the corresponding regions in the brain.

Although the invention has thus far been described in terms of a flexible, preformed structure having flange portions which are adapted to overlie a hardenable paste placed over the mandibular premolar teeth, it is envisaged that the orthopedic appliance could be constructed in other ways.

The first alternate way in which the orthopedic appliance could be constructed involves forming the complete appliance from a class of thermoplastic resin which is mouldable under pressure at an elevated temperature. Such mouldable thermoplastic resins have become popular in constructing mouth guards for athletic contestants. Canadian Pat. No. 782,188 describes the construction of such a mouth guard. As applied to this construction of the orthopedic appliance, the preformed structure would have integral thickened mouldable pads as the flange portions and there would be no need to utilize a hardenable paste. The preformed structure of thermoplastic resin would be heated to within the temperature range in which it is mouldable and then placed into the patient's mouth; the patient would bite into the preformed structure while still mouldable to place therein an impression of his upper and lower molar or premolar teeth, or both.

A further alternative form of the orthopedic appliance could comprise a resilient, preformed acrylic structure as in the preceding main embodiment and would further comprise mouldable inserts of thermoplastic resin, as in the immediately preceding embodiment, which inserts would be bonded to the flanges of the preformed structure prior to its placement in the patient's mouth. Once bonded to the preformed structure, the mouldable inserts would be heated to within the temperature range in which they are mouldable and then the appliance quickly placed into the patient's mouth. The patient would then bite into the inserts to place therein the surface contour of the upper and lower molar or premolar teeth, or both.

I claim:

1. An orthopedic appliance for relieving maxillo-mandibular imbalance, comprising:
 a flexible, preformed structure having an arcuate first portion adapted to extend along and be adjacent to the surface of the mandibular teeth, and two flange portions each integrally connected to a respective end section of the first portion and adapted to overlie the tops of a respective set of either the mandibular premolar teeth or the mandibular molar teeth, or both, and
 two moulded inserts, each bonded to a respective one of the flange portions and adapted to extend from that flange portion toward the respectively associated set of mandibular teeth, each insert having a surface contour corresponding to that on the respectively associated set of mandibular teeth, said flange portions and moulded inserts, in use, being disposed between such set of mandibular teeth and the corresponding teeth in the upper jaw, and providing a selected spacing between the mandible and the upper jaw, and, over an extended period of use, providing for stabilization and normalization of the position of the mandible relative to the upper jaw.

2. An orthopedic appliance for relieving maxillo-mandibular imbalance, comprising:
 a flexible, preformed structure having an arcuate first portion adapted to extend along and be adjacent to the surface of the mandibular teeth, and two flange portions, each integrally connected to a respective end section of the first portion and adapted to overlie the tops of a respective set of either the mandibular premolar teeth or the mandibular molar teeth, or both, and
 two mouldable inserts, each bonded to a respective one of the flange portions and adapted to extend from that flange portion toward the respectively associated set of mandibular teeth, each insert adapted to be moulded under pressure to create therein a surface contour corresponding to that on the respectively associated set of mandibular teeth, said flange portions and mouldable inserts, when adapted for use, being disposed between such set of mandibular teeth and the corresponding teeth in the upper jaw, and providing a selected spacing between the mandible and the upper jaw, and, over an extended period of use, providing for stabilization and normalization of the position of the mandible relative to the upper jaw.

3. An orthopedic appliance for relieving maxillo-mandibular imbalance, comprising:
 a flexible, preformed structure having an arcuate first portion adapted to extend along and be adjacent to the surface of the mandibular teeth, and two flange portions each integrally connected to a respective end section of the first portion and adapted to overlie the tops of a respective set of either the mandibular premolar teeth or the mandibular molar teeth, or both, two moulded inserts, each bonded to a respective one of the flange portions and adapted to extend from that flange portion toward the respectively associated set of mandibular teeth, each insert having a surface contour corresponding to that on the respectively associated set of mandibular teeth, and two additional moulded inserts, each bonded to a respective one of the flange portions and adapted to extend from that flange portion toward the respectively associated set of teeth in the upper jaw, each additional insert having a surface contour corresponding to that on the respectively associated set of teeth in the upper jaw, said flange portions, moulded inserts, and additional moulded inserts, in use, being disposed between such set of mandibular teeth and the corresponding teeth in the upper jaw, and providing a selected spacing between the mandible and the upper jaw, and, over an extended period of use, providing for stabilization and normalization of the position of the mandible relative to the upper jaw.

4. The orthopedic appliance of claim 1, 2, or 3, wherein the arcuate first portion of the preformed structure extends along the inner surface of the mandibular teeth.

5. The orthopedic appliance of claim 1, 2, or 3, wherein the preformed structure is of a unitary size and shape adapted to fit all wearers.

6. The orthopedic appliance of claim 1, 2, or 3, wherein the preformed structure is formed from acrylic.

7. An orthopedic appliance for relieving maxillo-mandibular imbalance, comprising:

a flexible, preformed structure having an arcuate first portion adapted to extend along and be adjacent to the surface of the mandibular teeth, and two flange portions, each integrally connected to a respective end section of the first portion and adapted to overlie the tops of a respective set of either the mandibular premolar teeth or the mandibular molar teeth, or both, two mouldable inserts, each bonded to a respective one of the flange portions and adapted to extend from that flange portion toward the respectively associated set of mandibular teeth, each insert adapted to be moulded under pressure to create therein a surface contour corresponding to that on the respectively associated set of mandibular teeth, and two additional mouldable inserts, each bonded to a respective one of the flange portions and adapted to extend from that flange portion toward the respectively associated set of teeth in the upper jaw, each additional insert adapted to be moulded under pressure to create therein a surface contour corresponding to that on the respectively associated set of teeth in the upper jaw, said flange portions, mouldable inserts, and additional mouldable inserts, when adapted for use, being disposed between such set of mandibular teeth and the corresponding teeth in the upper jaw, and providing a selected spacing between the mandible and the upper jaw, and, over an extended period of use, providing for stabilization and normalization of the position of the mandible relative to the upper jaw.

8. An orthopedic appliance for relieving maxillo-mandibular imbalance, comprising:

a mouldable structure having an arcuate first portion adapted to extend along and be adjacent to the surface of the mandibular teeth, and two flange portions, each integrally connected to a respective end section of the first portion and adapted to overlie the tops of a respective set of either the mandibular premolar teeth or the mandibular molar teeth, or both, each flange portion being adapted to be moulded by closing of the jaws to create in the flange portion a surface contour corresponding to that on the respectively associated set of mandibular teeth, said flange portions, when adapted for use, being disposed between such set of mandibular teeth and the corresponding teeth in the upper jaw, and providing a selected spacing between the mandible and the upper jaw, and, over an extended period of use, providing for stabilization and normalization of the position of the mandible relative to the upper jaw.

9. An orthopedic appliance for relieving maxillo-mandibular imbalance, comprising:

a mouldable structure having an arcuate first portion adapted to extend along and be adjacent to the surface of the mandibular teeth, and two flange portions, each integrally connected to a respective end section of the first portion and adapted to overlie the tops of a respective set of either the mandibular premolar teeth or the mandibular molar teeth, or both, each flange portion being adapted to be moulded by closing of the jaws to create on one surface of the flange portion a surface contour corresponding to that on the respectively associated set of mandibular teeth and on an opposite surface of the flange portion a surface contour corresponding to that on the respectively associated set of teeth in the upper jaw, such flange portions, when adapted for use, being disposed between such set of mandibular teeth and the corresponding teeth in the upper jaw, and providing a selected spacing between the mandible and the upper jaw, and, over an extended period of use, providing for stabilization and normalization of the position of the mandible relative to the upper jaw.

10. The orthopedic appliance of claim 7, 8, or 9, wherein the arcuate first portion of the mouldable structure extends along the inner surface of the mandibular teeth.

11. The orthopedic appliance of claim 7, 8, and 9, wherein the mouldable structure, prior to moulding, is of a unitary size and shape adapted to fit all wearers.

12. The orthopedic appliance of claim 7, 8 or 9, wherein the mouldable structure is formed from thermoplastic resin mouldable under pressure at an elevated temperature.

13. A method for relieving maxillo-mandibular imbalance by repositioning of the lower jaw relative to the upper jaw, comprising the steps of:

spreading a malleable polymer mixture onto the flange portions of a flexible, preformed structure having an arcuate first portion and two flange portions, each flange portion being integrally connected to a respective end section of the first portion;

inserting the preformed structure between the jaws, the structure being positioned such that the arcuate first portion extends along and is adjacent to the surface of the mandibular teeth and the malleable polymer mixture on each flange portion rests on a respective set of the mandibular premolar teeth or the mandibular molar teeth, or both;

closing the jaws to conform the shape of the malleable polymer mixture to the shape of the biting surfaces of the respective sets of mandibular teeth and to promote bonding between the preformed structure and the malleable polymer mixture;

removing the preformed structure with the malleable polymer mixture bonded thereto after commencement of hardening of the mixture, the mixture surfaces retaining the contour of the biting surfaces of the respective sets of mandibular teeth; and periodically reinserting the structure between the jaws to rest on the respective sets of mandibular teeth after hardening of the mixture.

14. A method for relieving maxillo-mandibular imbalance by repositioning of the lower jaw relative to the upper jaw, comprising the steps of:

spreading a malleable polymer mixture over each set of mandibular premolar teeth or mandibular molar teeth, or both;

inserting a flexible, preformed structure between the jaws, the structure having an arcuate first portion and two flange portions, each flange portion being integrally connected to a respective end section of the first portion, the structure being positioned such that the arcuate first portion extends along and is adjacent to the surface of the mandibular teeth and each flange portion rests on the malleable polymer mixture over a respective set of the mandibular teeth;

closing the jaws to conform the shape of the malleable polymer mixture to the shape of the biting surfaces of the respective sets of mandibular teeth and to promote bonding between the preformed structure and the malleable polymer mixture;

removing the preformed structure with the malleable polymer mixture bonded thereto after commencement of hardening of the mixture, the mixture surfaces retaining the contour of the biting surfaces of the respective sets of mandibular teeth; and periodically reinserting the structure between the jaws to rest on the respective sets of mandibular teeth after hardening of the mixture.

15. A method for relieving maxillo-mandibular imbalance as in claim 13 or 14, wherein the arcuate first portion of the preformed structure extends along the inner surface of the mandibular teeth during use.

16. A method for relieving maxillo-mandibular imbalance as in claim 13 or 14, wherein the preformed structure is of a unitary size and shape adapted to fit all wearers.

17. A method for relieving maxillo-mandibular imbalance as in claim 13 or 14, wherein the preformed structure is formed from acrylic.

18. A method for relieving maxillo-mandibular imbalance as in claim 17, and, prior to the step of periodically reinserting the structure between the jaws, additionally comprising the steps of:

spreading a further amount of the malleable polymer mixture onto the other side of each flange portion of the flexible, preformed structure from that side on which polymer mixture was first placed;

closing the jaws to conform the shape of the further amount of the malleable polymer mixture to the shape of the biting surfaces of the corresponding teeth on the upper jaw and to promote bonding between the preformed structure and the further amount of the malleable polymer mixture; and, removing the preformed structure with the further amount of the malleable polymer mixture bonded thereto after commencement of hardening of that further amount of mixture, the surfaces of that further amount of mixture retaining the contour of the biting surfaces of the corresponding teeth on the upper jaw.

19. A method for relieving maxillo-mandibular imbalance as in claim 18, and, prior to the step of periodically reinserting the structure between the jaws, additionally comprising the steps of:

spreading a further amount of the malleable polymer mixture onto the other side of each flange portion of the flexible, preformed structure from that side on which polymer mixture was first placed;

closing the jaws to conform the shape of the further amount of the malleable polymer mixture to the shape of the biting surfaces of the corresponding teeth on the upper jaw and to promote bonding between the preformed structure and the further amount of the malleable polymer mixture; and, removing the preformed structure with the further amount of the malleable polymer mixture bonded thereto after commencement of hardening of that further amount of mixture, the surfaces of that further amount of mixture retaining the contour of the biting surfaces of the corresponding teeth on the upper jaw.

20. A method for relieving maxillo-mandibular imbalance as in claim 18 or 19, wherein the arcuate first portion of the preformed structure extends along the inner surface of the mandibular teeth during use.

21. A method for relieving maxillo-mandibular imbalance as in claim 18 or 19, wherein the preformed structure is of a unitary size and shape adapted to fit all wearers.

22. A method for relieving maxillo-mandibular imbalance as in claim 18 or 19, wherein the preformed structure is formed from acrylic.

* * * * *